(12) United States Patent
Iwasaki

(10) Patent No.: US 9,664,604 B2
(45) Date of Patent: May 30, 2017

(54) MEASUREMENT APPARATUS, MEASUREMENT METHOD, AND METHOD OF MANUFACTURING ARTICLE

(71) Applicant: CANON KABUSHIKI KAISHA, Tokyo (JP)

(72) Inventor: Yasushi Iwasaki, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 464 days.

(21) Appl. No.: 14/477,331

(22) Filed: Sep. 4, 2014

(65) Prior Publication Data

US 2015/0073740 A1 Mar. 12, 2015

(30) Foreign Application Priority Data

Sep. 9, 2013 (JP) ................. 2013-186578

(51) Int. Cl.
| | |
|---|---|
| *G06F 19/00* | (2011.01) |
| *G01N 3/56* | (2006.01) |
| *G01B 9/02* | (2006.01) |
| *G01B 7/012* | (2006.01) |
| *G01B 7/28* | (2006.01) |
| *G01B 11/00* | (2006.01) |

(52) U.S. Cl.
CPC ............ *G01N 3/56* (2013.01); *G01B 7/012* (2013.01); *G01B 7/28* (2013.01); *G01B 9/02027* (2013.01); *G01B 11/007* (2013.01)

(58) Field of Classification Search
CPC .... G01B 21/045; B82Y 35/00; G01Q 30/025; G01Q 70/02

USPC ................................. 702/94, 182–185
See application file for complete search history.

(56) References Cited

U.S. PATENT DOCUMENTS

| 6,057,547 A * | 5/2000 | Park ................. B82Y 35/00 850/10 |
|---|---|---|
| 2005/0111725 A1* | 5/2005 | Noda ................. G01B 21/045 382/141 |
| 2014/0267623 A1* | 9/2014 | Bridges ............... G01S 17/003 348/46 |
| 2016/0143517 A1* | 5/2016 | Vance ............... A61B 1/00096 600/177 |

FOREIGN PATENT DOCUMENTS

JP 5269649 A 10/1993

* cited by examiner

*Primary Examiner* — Edward Raymond
(74) *Attorney, Agent, or Firm* — Rossi, Kimms & McDowell LLP

(57) ABSTRACT

The present invention provides a measurement apparatus which includes a probe having a leading edge portion configured to come into contact with a surface to be measured and a holding portion configured to hold the leading edge portion, and measures a shape of the surface by scanning the probe relative to the surface in a state in which the leading edge portion and the surface are in contact, comprising a processing unit configured to correct measurement data at a measurement point on the surface based on data of a scanning distance of the probe and information about abrasion of the leading edge portion caused by scanning of the probe.

13 Claims, 7 Drawing Sheets

F I G. 2
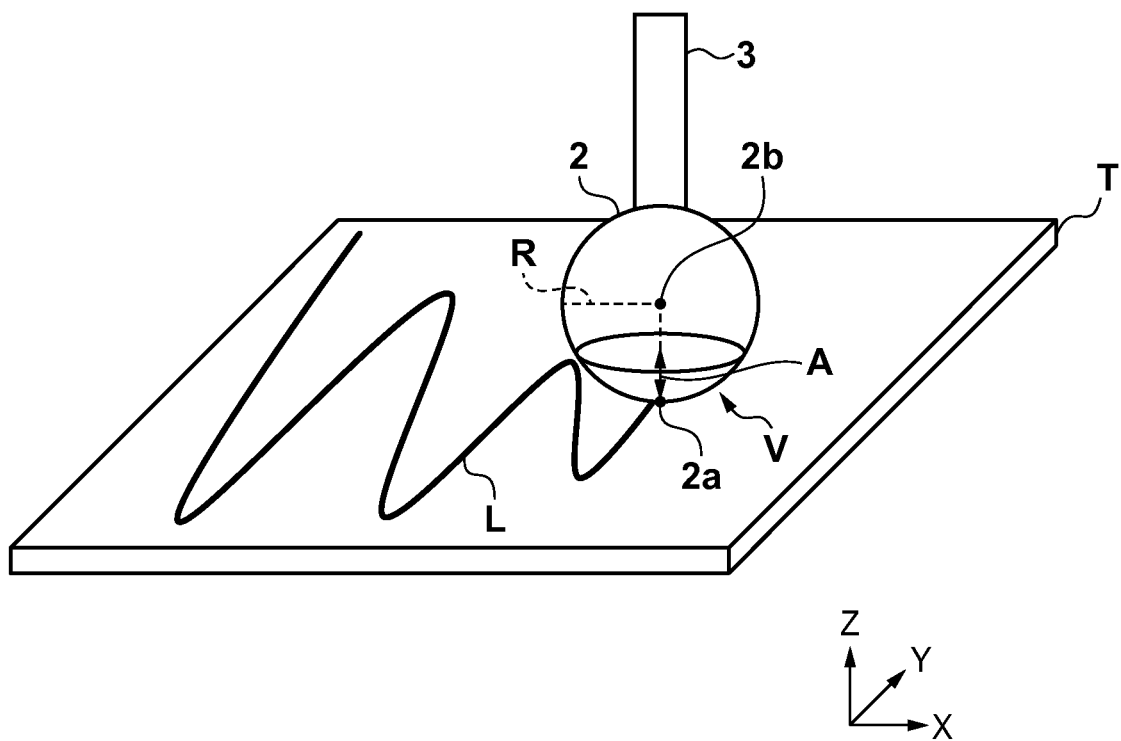

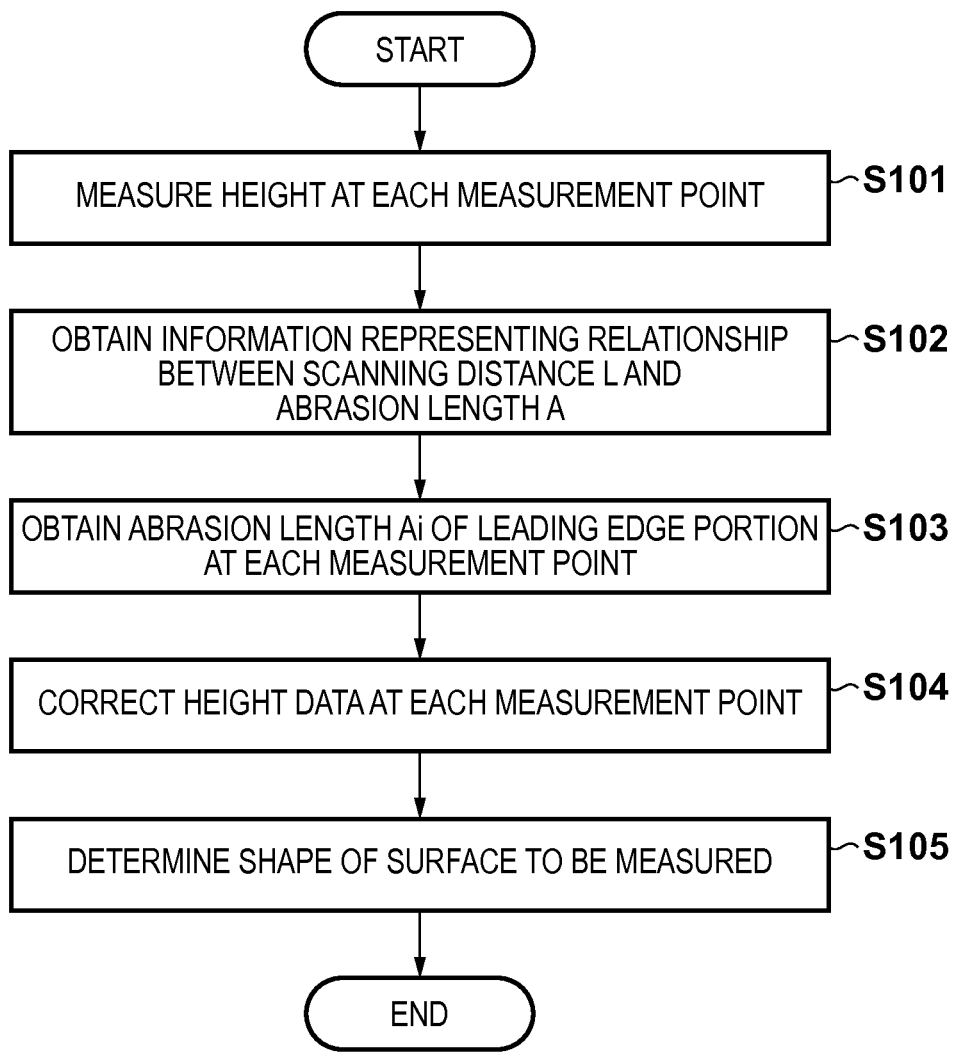

F I G. 4A
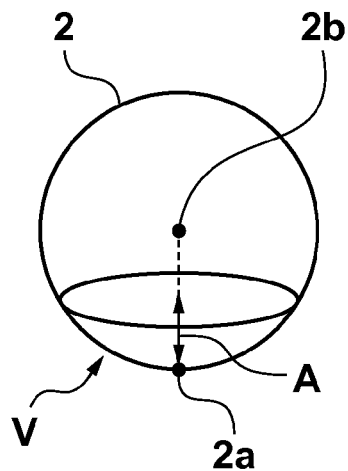
F I G. 4B
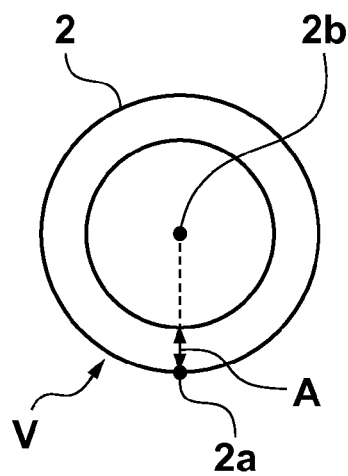
F I G. 4C
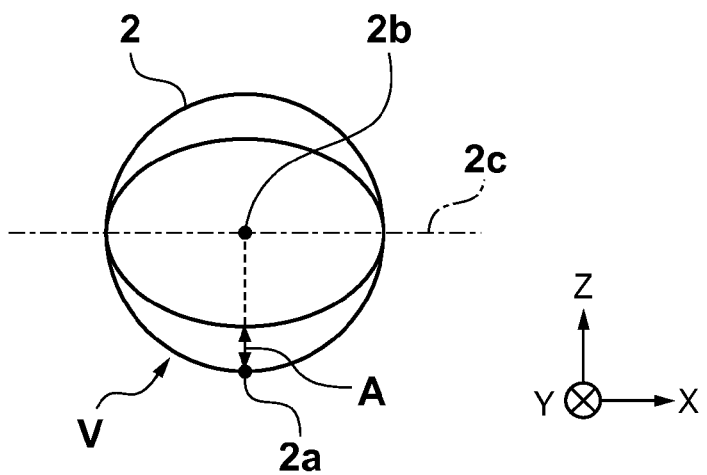

MEASUREMENT APPARATUS, MEASUREMENT METHOD, AND METHOD OF MANUFACTURING ARTICLE

BACKGROUND OF THE INVENTION

Field of the Invention

The present invention relates to a measurement apparatus, a measurement method, and a method of manufacturing an article.

Description of the Related Art

There is known a contact measurement apparatus that measures the shape of a surface to be measured out of a lens, a mirror, or the like while bringing the leading edge portion of a probe into contact with the surface to be measured. The contact measurement apparatus can measure the shape of the surface to be measured by scanning the probe relative to the surface to be measured in a state in which the leading edge portion of the probe and the surface to be measured are in contact.

Such a contact measurement apparatus scans the probe in the state in which the leading edge portion of the probe is in contact with the surface to be measured. For this reason, the leading edge portion of the probe may abrade as the probe is scanned, resulting in a measurement error. In Japanese Patent Laid-Open No. 5-269649, a method in which a measurement error caused by abrasion of the leading edge portion of a probe is obtained in advance using a reference work, and the measurement result of the shape of a surface to be measured is corrected using the measurement error obtained using the reference work as a correction value is proposed.

Since the method described in Japanese Patent Laid-Open No. 5-269649 obtains the correction value to be used to correct the measurement result of the shape of a surface to be measured using a reference work, the step of correcting the measurement result can be cumbersome.

SUMMARY OF THE INVENTION

The present invention provides, for example, a technique advantageous in accurately measuring the shape of a surface to be measured.

According to one aspect of the present invention, there is provided a measurement apparatus which includes a probe having a leading edge portion configured to come into contact with a surface to be measured and a holding portion configured to hold the leading edge portion, and measures a shape of the surface by scanning the probe relative to the surface in a state in which the leading edge portion and the surface are in contact, comprising: a processing unit configured to correct measurement data at a measurement point on the surface based on data of a scanning distance of the probe and information about abrasion of the leading edge portion caused by scanning of the probe.

Further features of the present invention will become apparent from the following description of exemplary embodiments with reference to the attached drawings.

BRIEF DESCRIPTION OF THE DRAWINGS

FIG. 2 is a view showing a state in which a probe is scanned;

FIG. 3 is a flowchart showing a method of measuring the shape of a surface to be measured in the first embodiment;

FIG. 4A is a view showing an abrasion model of a leading edge portion;

FIG. 4B is a view showing another abrasion model of the leading edge portion;

FIG. 4C is a view showing still another abrasion model of the leading edge portion;

DESCRIPTION OF THE EMBODIMENTS

Figure 1:
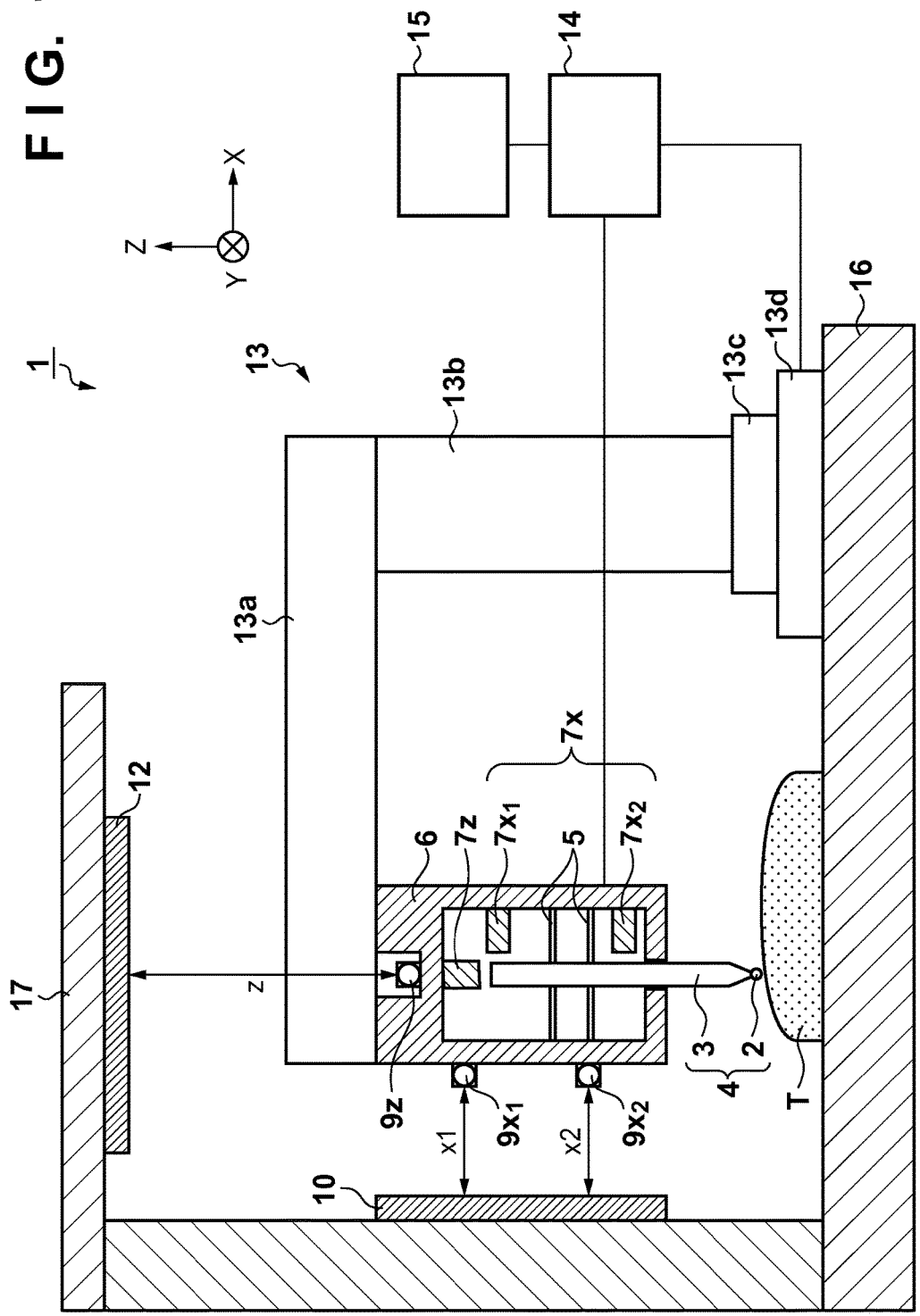
FIG. 1 is a view showing a measurement apparatus according to the first embodiment.

Exemplary embodiments of the present invention will be described below with reference to the accompanying drawings. Note that the same reference numerals denote the same members throughout the drawings, and a repetitive description thereof will not be given.

First Embodiment

A measurement apparatus 1 according to the first embodiment of the present invention will be described with reference to FIG. 1. FIG. 1 is a view showing the measurement apparatus 1 according to the first embodiment. The measurement apparatus 1 according to the first embodiment includes a probe 4, a probe housing 6 that elastically supports the probe 4, a driving unit 13 that drives the probe housing 6, a control unit 14, and a processing unit 15. The control unit 14 includes a CPU and a memory, and controls movement of the probe 4 and measurement of the shape of a surface to be measured (surface of an object T to be measured). The processing unit 15 includes a CPU and a memory, and corrects the measurement result of the shape of the surface to be measured. The measurement apparatus 1 having the above arrangement can measure the shape of the surface to be measured by scanning the probe 4 relative to the surface to be measured in a state in which a leading edge portion 2 of the probe 4 is in contact with the surface to be measured.

The probe 4 has the leading edge portion 2 that is brought into contact with the surface to be measured when measuring its shape, and a holding portion 3 that holds the leading edge portion 2. The leading edge portion 2 is formed from, for example, a precise ball having high sphericity. The probe 4 is elastically supported by the probe housing 6 via a support member 5. The probe housing 6 includes a first detection unit $7x$ that detects a displacement of the probe 4 in the X direction, a second detection unit (not shown) detects a displacement of the probe 4 in the Y direction, and a third detection unit $7z$ that detects a displacement of the probe 4 in the Z direction.

In the first embodiment, as shown in FIG. 1, the first detection unit $7x$ is arranged on, for example, an X-direction plane in the probe housing 6, and includes two displacement meters $7x_1$ and $7x_2$ arranged away from each other in the Z direction. Each of the displacement meters $7x_1$ and $7x_2$ includes, for example, a capacitance sensor. They measure a change in the capacitance between the probe 4 and the displacement meter $7x_1$ and a change in the capacitance between the probe 4 and the displacement meter $7x_2$, respectively. The first detection unit $7x$ can thus detect the displacement amount of the probe 4 in the X direction based on the measurement result of the displacement meter $7x_1$ and the measurement result of the displacement meter $7x_2$. In the first embodiment, the second detection unit that detects a displacement of the probe 4 in the Y direction can have the same arrangement as the first detection unit $7x$.

The third detection unit $7z$ includes a displacement meter arranged on a Z-direction plane in the probe housing 6. The displacement meter includes, for example, a capacitance sensor, and measures a change in the capacitance between the probe 4 and the displacement meter. The third detection unit $7z$ can thus detect the displacement amount of the probe 4 in the Z direction based on the measurement result of the displacement meter. Each of the displacement meters included in the first detection unit $7x$, the second detection unit (not shown), and the third detection unit $7z$ according to the first embodiment includes a capacitance sensor. However, the present invention is not limited to this, and any arrangement capable of accurately detecting the displacement amount of the probe 4 is usable.

The driving unit 13 is arranged on a base 16, and provided to drive the probe housing 6. The driving unit 13 includes, for example, a top plate 13a that supports the probe housing 6, a Z-axis stage 13b that drives the top plate 13a in the Z direction, a Y-axis stage 13c that drives the top plate 13a in the Y direction, and an X-axis stage 13d that drives the top plate 13a in the X direction. This makes it possible to drive the probe housing 6 in the three axial directions and scan the probe 4 elastically supported by the probe housing 6 relative to the surface to be measured in a state in which the leading edge portion 2 of the probe 4 and the surface to be measured are in contact.

The probe housing 6 includes interferometers $9x_1$ and $9x_2$ configured to measure the X-direction position of the probe housing 6, an interferometer (not shown) configured to measure the Y-direction position, and an interferometer $9z$ configured to measure the Z-direction position. Each interferometer $9x_1$ or $9x_2$ irradiates, for example, an X reference mirror 10 supported by a structure 17 connected to the base 16, and a reference surface provided inside with laser beams. Each interferometer $9x_1$ or $9x_2$ can detect a displacement of the probe housing 6 from a reference position by interference between the laser beam reflected by the X reference mirror 10 and the laser beam reflected by the reference surface. This makes it possible to measure the distance between the X reference mirror 10 and the probe housing 6, that is, the X-direction position of the probe housing 6. The interferometer $9z$ irradiates, for example, a Z reference mirror 12 supported by the structure 17, and a reference surface provided inside with laser beams. The interferometer $9z$ can detect a displacement of the probe housing 6 from the reference position by interference between the laser beam reflected by the Z reference mirror 12 and the laser beam reflected by the reference surface. This makes it possible to measure the distance between the Z reference mirror 12 and the probe housing 6, that is, the Z-direction position of the probe housing 6. The interferometer configured to measure the Y-direction position of the probe housing 6 has the same arrangement as the interferometer $9x_1$ or $9x_2$ configured to measure the X-direction position of the probe housing 6, and a description thereof will be omitted here.

The measurement apparatus 1 having the above arrangement scans the probe 4 relative to the surface to be measured in a state in which the leading edge portion 2 and the surface to be measured are in contact, and measures a height at each of a plurality of measurement points on the surface to be measured. The measurement apparatus 1 can thus determine the shape of the surface to be measured based on the measured height data at each measurement point. However, since the measurement apparatus 1 scans the probe 4 in the state in which the leading edge portion 2 of the probe 4 and the surface to be measured are in contact, the leading edge portion 2 of the probe 4 may abrade as the probe 4 is scanned, resulting in a measurement error. To prevent this, the measurement apparatus 1 according to the first embodiment calculates an abrasion length A of the leading edge portion 2 in accordance with a scanning distance L representing the accumulated distance value (for example, the distance upon scanning the probe 4 on a plurality of surfaces to be measured) accumulated upon scanning the probe 4 in a state in which the leading edge portion 2 abrades. The measurement apparatus 1 corrects the height data at each measurement point using the calculated abrasion length A as a correction value, and determines the shape of the surface to be measured based on the corrected height data at each measurement point. This allows the measurement apparatus 1 to accurately measure the shape of the surface to be measured. As shown in FIG. 2, the abrasion length A is the amount of a change, caused by abrasion of the leading edge portion 2, in the distance between a contact point 2a of the leading edge portion 2 in contact with the surface to be measured and a reference point of the leading edge portion 2 (a center 2b of the leading edge portion 2, in the first embodiment). In the first embodiment, the step of correcting the measurement result of the shape of the surface to be measured is assumed to be executed by the processing unit 15 included in the measurement apparatus 1. However, the present invention is not limited to this, and the step may be executed by, for example, a computer outside the measurement apparatus 1.

A method of measuring the shape of a surface to be measured by scanning the probe 4 in a state in which the leading edge portion 2 and the surface to be measured are in contact will be described below with reference to FIG. 3. FIG. 3 is a flowchart showing the method of measuring the shape of the surface to be measured.

In step S101, the processing unit 15 scans the probe 4 in the state in which the leading edge portion 2 and the surface to be measured are in contact, and causes the control unit 14 to measure the height at each measurement point (coordinates $(X_i, Y_i)$). The processing unit 15 stores measurement data (position coordinates $(X_i, Y_i, Z_i)$) at each measurement point together with a scanning distance $L_i$ upon scanning the probe 4 until the measurement at the measurement point. For example, when the number of measurement points is n, n data $(X_i, Y_i, Z_i, L_i)$ are stored in the processing unit 15. That is, data $(X_1, Y_1, Z_1, L_1), \ldots, (X_n, Y_n, Z_n, L_n)$ at the respective measurement points are stored in the processing unit 15. The scanning distance $L_i$ at each measurement point can be calculated using, for example, the measurement data (position coordinates $(X_i, Y_i, Z_i)$) at each measurement point. Alternatively, the scanning distance $L_i$ may be obtained by a mechanism configured to measure the scanning distance $L_i$ and provided in the measurement apparatus 1. Step S101 may be performed after step S102 to be described later.

In step S102, the processing unit 15 obtains information representing the relationship between the scanning distance L and the abrasion length A. As described above, the scanning distance L is the accumulated distance value accumulated upon scanning the probe 4 relative to the surface to be measured in a state in which the leading edge portion 2 of the probe 4 abrades, for example, the distance upon scanning the probe 4 on a plurality of surfaces to be measured. The relationship between the scanning distance L and the abrasion length A is obtained by, for example, experiments or calculations.

A method of obtaining the relationship between the scanning distance L and the abrasion length A by experiments will be described first. To obtain the relationship by an experiment, for example, the probe 4 is scanned by only a scanning distance $L_1$, and an abrasion length $A_1$ of the leading edge portion 2 at that time is measured. In addition, the probe 4 is scanned by only a scanning distance $L_2$, and an abrasion length $A_2$ of the leading edge portion 2 at that time is measured. By repeating this step, data of a plurality of sets of the scanning distances L and the abrasion lengths A can be obtained, and a discrete relationship between the scanning distance L and the abrasion length A can be obtained. When complementary processing is performed for the obtained discrete relationship between the scanning distance L and the abrasion length A, a continuous relationship between the scanning distance L and the abrasion length A can be obtained.

A method of obtaining the relationship between the scanning distance L and the abrasion length A by calculations will be described next. According to the Holm-Archard theory that is a theory concerning abrasion, an abrasion volume V (see FIG. 2) representing the abraded volume of the leading edge portion 2 of the probe 4 can be given by $$V = KWL/H \quad (1)$$

where K is the proportionality constant, W is the load applied to the probe 4, L is the scanning distance, and H is the hardness of the leading edge portion 2 of the probe 4. The load W is kept constant by controlling the pressure applied to the probe 4, and the hardness H of the leading edge portion 2 also remains unchanged. Hence, by handling the load W and the hardness H as constants, equation (1) can be rewritten as $$V = KL \quad (2)$$

When the leading edge portion 2 has a spherical shape and is fixed to the holding portion 3, the leading edge portion 2 abrades from the contact point 2a in contact with the surface to be measured toward the center 2b of the leading edge portion 2, as shown in FIG. 4A. In this abrasion model of the leading edge portion 2, the abrasion volume V can be calculated by $$V = \frac{1}{3}\pi A^2 (3R - A) \quad (3)$$

where A is the abrasion length, and R is the radius of the leading edge portion 2.

Using equations (2) and (3), the proportionality constant K can be given by $$K = \frac{1}{3L}\pi A^2 (3R - A) = \frac{1}{3L_0}\pi A_0^2 (3R - A_0) \quad (4)$$

The proportionality constant K is determined by substituting, into equation (4), a scanning distance $L_0$ and an abrasion length $A_0$ on at least one point of the surface to be measured when the probe 4 is scanned from the initial point on the surface to be measured through the at least one point. The scanning distance $L_0$ and the abrasion length $A_0$ can be obtained by conducting experiments of scanning the probe 4 in the state in which the leading edge portion 2 is in contact with the surface to be measured.

After determining the proportionality constant K, a cubic equation concerning the abrasion length A is set up using equations (2) and (3), as indicated by $$A = R - \frac{(1 - i\sqrt{3})\pi^{1/3}R^2}{2^{2/3}(-KL + 2\pi R^3 + \sqrt{3}\sqrt{3K^2L^2 - 4KL\pi R^3})^{1/3}} - \frac{(1 - i\sqrt{3})(-3KL + 2\pi R^3 + \sqrt{3}\sqrt{3K^2L^2 - 4KL\pi R^3})^{1/3}}{2(2\pi)^{1/3}} \quad (5)$$

For a cubic equation, a formula of solution is known in general. The relationship between the abrasion length A and the scanning distance L can be obtained by applying the formula. In this case, to the abrasion length A, a condition $0 \leq A \leq 2R$ (2R is the diameter of the leading edge portion 2) is applied. In equation (5), i is the imaginary unit. However, since the imaginary part of a complex number is zero, a real number is represented by the equation as a whole.

Figure 5:
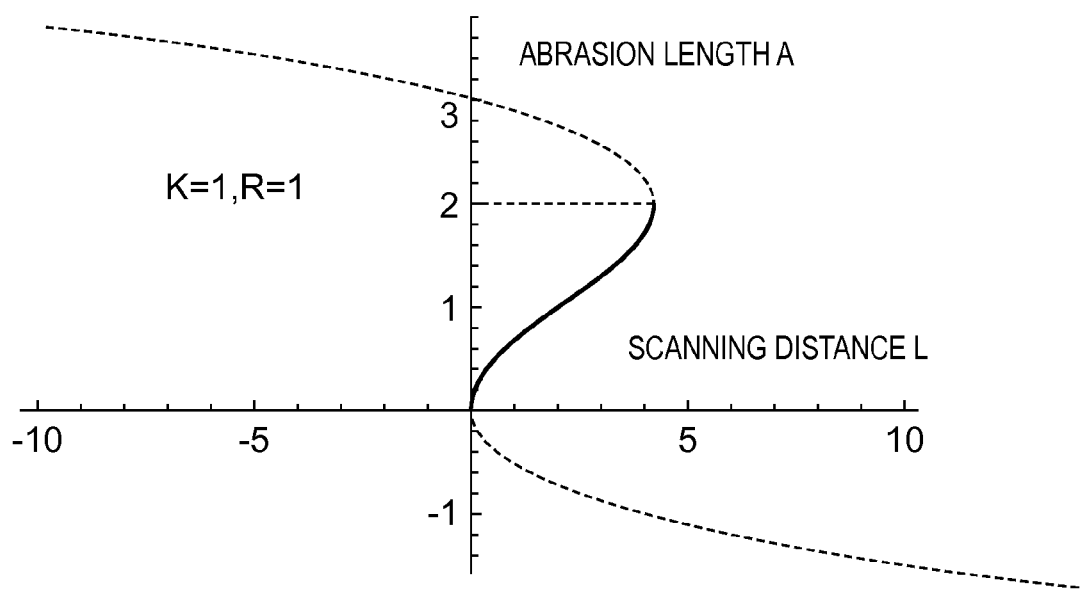
FIG. 5 is a graph showing an example of the relationship between a scanning distance L and an abrasion length A.

FIG. 5 is a graph showing an example of the relationship between the scanning distance L and the abrasion length A. In FIG. 5, the relationship is calculated by setting the proportionality constant K and the radius R of the leading edge portion 2 to 1. In fact, the proportionality constant K calculated using equation (4) and the radius R of the leading edge portion as the design value or measured value of the leading edge portion 2 are used. Referring to FIG. 5, a portion indicated by the thin line meets the condition $0 \leq A \leq 2R$.

In step S103, the processing unit 15 obtains an abrasion length $A_i$ at each measurement point from the scanning distance $L_i$ at each measurement point based on the relationship (equation (5)) between the scanning distance L and the abrasion length A obtained in step S102. For example, the processing unit 15 can obtain the abrasion length $A_i$ of the leading edge portion 2 when measuring at the ith measurement point by substituting the scanning distance $L_i$ at the ith measurement point into equation (5). The abrasion lengths $A_1, \ldots, A_n$ at the respective measurement points can be obtained by performing this calculation at each measurement point.

In step S104, the processing unit 15 corrects height data $Z_i$ at each measurement point using the abrasion length $A_i$ at each measurement point obtained in step S103. For example, the processing unit 15 corrects the height data $Z_i$ by adding the abrasion length $A_i$ at the ith measurement point to the height data $Z_i$ at the ith measurement point. The processing unit 15 can thus obtain corrected height data $Z_i'$. In step S105, the processing unit 15 determines the shape of the surface to be measured based on the position coordinates ($X_i$, $Y_i$, $Z_i'$) of each measurement point having the height data $Z_i'$ corrected in step S104. The measurement apparatus 1 can thus accurately measure the shape of the surface to be measured by executing steps S101 to S105.

In step S102 described above, since a case where the leading edge portion 2 is fixed to the holding portion 3 is assumed, the relationship between the scanning distance L and the abrasion length A is calculated using the abrasion model (FIG. 4A) corresponding to abrasion that progresses from the contact point 2a in contact with the surface to be measured toward the center 2b of the leading edge portion 2. In a case different from the case where the leading edge portion 2 is fixed to the holding portion 3, however, the relationship between the scanning distance L and the abrasion length A can be calculated using an abrasion model different from that shown in FIG. 4A. That is, the relationship between the scanning distance L and the abrasion length A can be obtained using an abrasion model corresponding to the state of the leading edge portion 2 held by the holding portion 3. For example, when the leading edge portion 2 has a spherical shape and is held by the holding portion 3 so as to rotate about the center 2b, the leading edge portion 2 abrades from its surface toward the center 2b, as shown in FIG. 4B. In this abrasion model of the leading edge portion 2, the abrasion volume V can be calculated by $$V = \frac{4}{3}\pi A(3R^2 - 3RA + A^2) \quad (6)$$

The relationship between the scanning distance L and the abrasion length A can be obtained using equations (2) and (6).

When the leading edge portion 2 has a spherical shape and is held by the holding portion 3 so as to rotate about an axis 2c passing through the center 2b, the leading edge portion 2 abrades from a portion of the surface far apart from the axis 2c, as shown in FIG. 4C. In this abrasion model of the leading edge portion 2, the abrasion volume V can be calculated by $$V = \frac{4}{3}\pi RA(2R - A) \quad (7)$$

The relationship between the scanning distance L and the abrasion length A can be obtained using equations (2) and (7).

As described above, the measurement apparatus 1 according to the first embodiment calculates the abrasion length A of the leading edge portion 2 in accordance with the scanning distance L upon scanning the probe 4 in a state in which the leading edge portion 2 abrades, and corrects the height data at each measurement point using the calculated abrasion length A as a correction value. The measurement apparatus 1 thus determines the shape of the surface to be measured based on the corrected height data at each measurement point. It is therefore possible to reduce measurement errors caused by abrasion of the leading edge portion 2 of the probe 4 and accurately measure the shape of the surface to be measured.

Second Embodiment

A measurement apparatus according to the second embodiment of the present invention will be described. In the first embodiment, a case has been described in which the contact point 2a in contact with the surface to be measured does not move on the surface of the leading edge portion 2, and abrasion progresses from a predetermined position of the surface of the leading edge portion 2 toward the center 2b of the leading edge portion 2, as shown in FIG. 4A. However, depending on the shape of the surface to be measured, for example, when the surface to be measured has a nonplanar shape, the contact point 2a in contact with the surface to be measured rarely stays at a predetermined position of the surface of the leading edge portion 2 but moves on the surface of the leading edge portion 2. In the second embodiment, a method of measuring the shape of a surface to be measured by scanning a probe 4 in a case where a contact point 2a moves on the surface of a leading edge portion 2 will be described with reference to FIG. 6. The apparatus arrangement of the measurement apparatus according to the second embodiment is the same as that of the measurement apparatus 1 according to the first embodiment, and a description thereof will be omitted.

Figure 6:
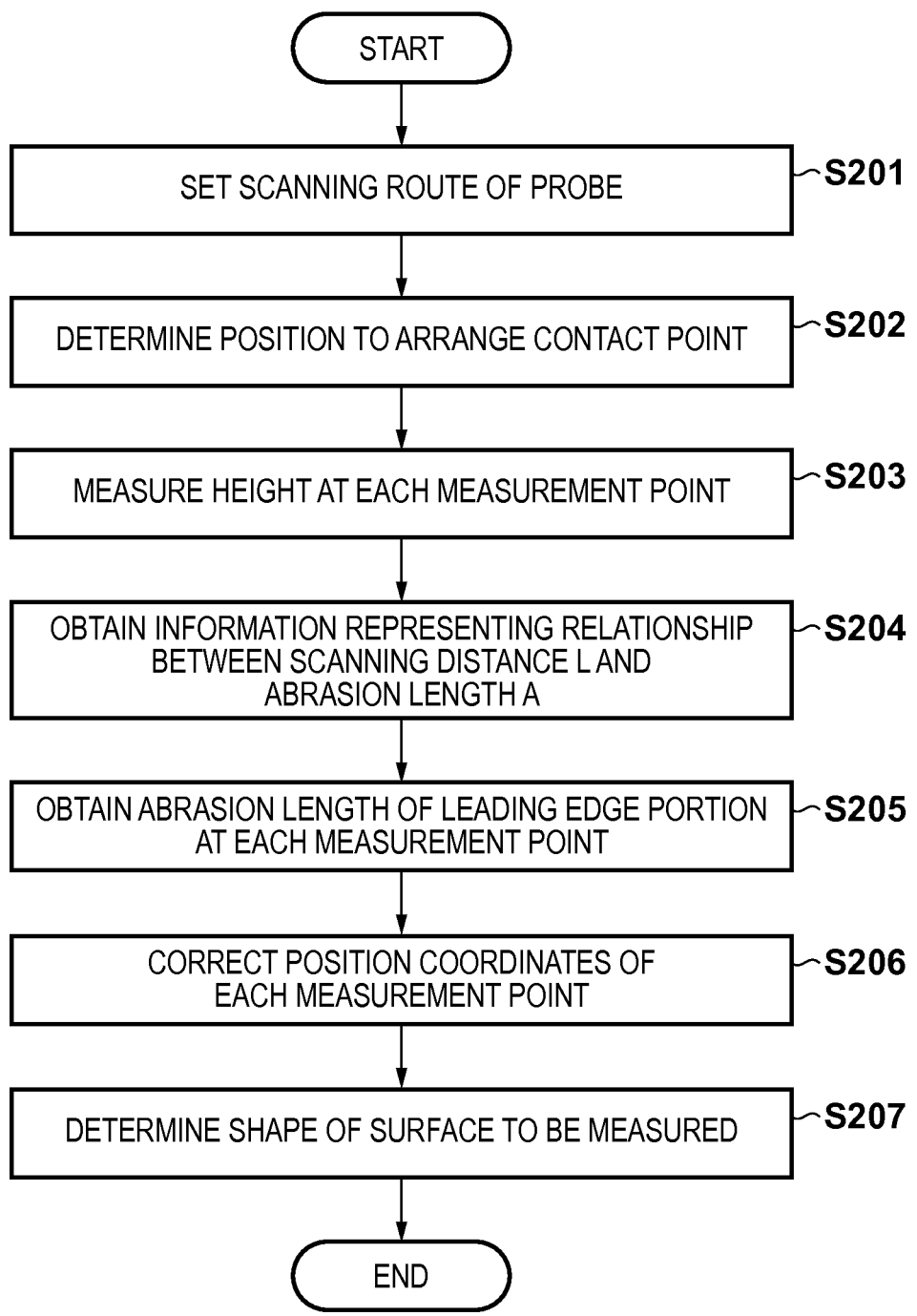
FIG. 6 is a flowchart showing a method of measuring the shape of a surface to be measured in the second embodiment.

FIG. 6 is a flowchart showing a method of measuring the shape of a surface to be measured. In step S201, a processing unit 15 sets a scanning route to scan the probe 4 on the surface to be measured. The scanning route can be set using, for example, the design data of the object to be measured, the rough shape of the surface be measured, which is measured by an external apparatus, or the like. After setting the scanning route, the processing unit 15 sets, on the scanning route, a plurality of measurement points where the height of the surface to be measured is to be measured. In step S202, the processing unit 15 determines a position on the surface of the leading edge portion 2 where the contact point 2a is to be arranged when measuring at each measurement point. The position on the surface of the leading edge portion 2 where the contact point 2a is to be arranged is determined for each measurement point using, for example, the design data of the surface to be measured, the rough shape of the surface be measured, which is measured by an external apparatus, or the like, assuming that the probe 4 does not abrade.

Figure 7:
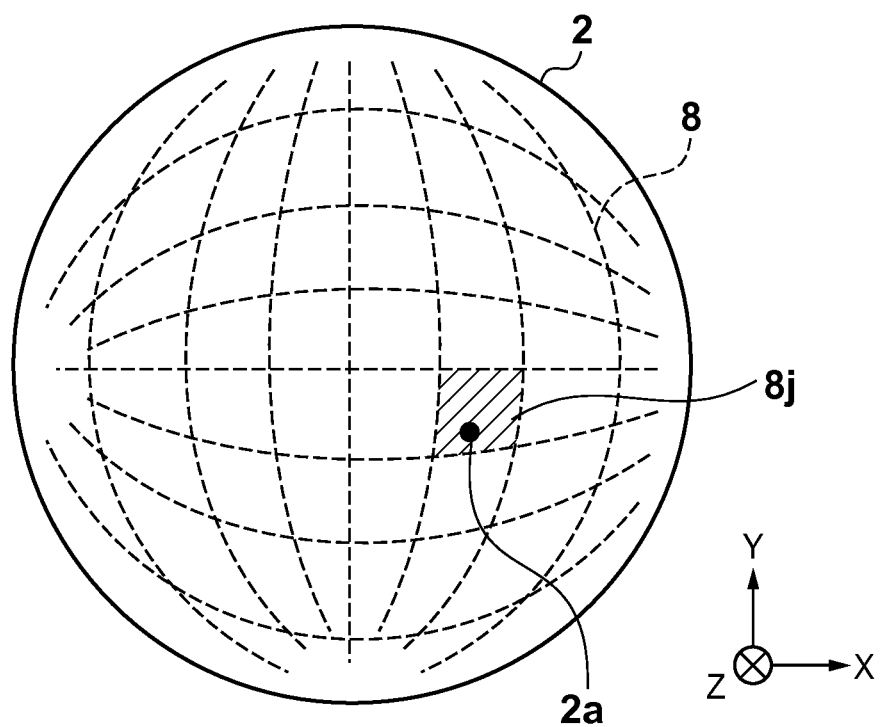
FIG. 7 is a view showing a leading edge portion viewed from the lower side (−Z direction).

In step S203, the processing unit 15 scans the probe 4 in a state in which the leading edge portion 2 and the surface to be measured are in contact, and causes a control unit 14 to measure the height at each measurement point (coordinates $(X_i, Y_i)$). The processing unit 15 stores measurement data (position coordinates $(X_i, Y_i, Z_i)$) at each measurement point together with a scanning distance $L_i$ upon scanning the probe 4 until the measurement at the measurement point. In the second embodiment, the surface of the leading edge portion 2 can be, for example, partitioned into a grid pattern, as shown in FIG. 7, and the scanning distance $L_i$ for each of a plurality of partitioned regions 8 can be stored. FIG. 7 is a view showing the leading edge portion viewed from the lower side (−Z direction). For example, assume a case where the position of the contact point 2a when measuring at the ith measurement point is located in a region 8j out of the plurality of regions 8. In this case, the processing unit 15 stores a scanning distance $L_{ij}$ representing the accumulated distance value accumulated upon scanning the probe 4 in a state in which abrasion occurs in the region 8j until the measurement at the ith measurement point together with the measurement data (position coordinates $(X_i, Y_i, Z_i)$) at the ith measurement point. That is, the processing unit 15 stores data $(X_i, Y_i, Z_i, L_{ij})$ at the ith measurement point.

In step S204, the processing unit 15 obtains information representing the relationship between a scanning distance L and an abrasion length A. The process of step S204 is the same in step S102 of FIG. 3, and a description thereof will be omitted. In step S205, the processing unit 15 obtains an abrasion length $A_{ij}$ in the region 8j from the scanning distance $L_{ij}$ in the region 8j where the contact point 2a is located at each measurement point based on the relationship between the scanning distance L and the abrasion length A obtained in step S204. For example, the processing unit 15 can obtain the abrasion length $A_{ij}$ of the leading edge portion 2 in the region 8j when measuring at ith the measurement point by substituting the scanning distance $L_1$ in the region 8j into equation (5). In step S206, the processing unit 15 corrects height data $Z_i$ at each measurement point using the abrasion length $A_{ij}$ in the region 8j obtained in step S205. For example, the processing unit 15 corrects the height data $Z_i$ by adding the abrasion length $A_{ij}$ in the region 8*j* at the ith measurement point to the height data $Z_i$ at the ith measurement point. The processing unit 15 can thus obtain corrected height data $Z_i'$. In the second embodiment, since the position of the contact point 2*a* on the surface of the leading edge portion 2 changes for each measurement point, the coordinates $(X_i, Y_i)$ of each measurement point can also be corrected using the position of the contact point 2*a* and the abrasion length $A_{ij}$ in the region 8*j*. The corrected coordinates $(X_i, Y_i)$ will be expressed as coordinates $(X_i', Y_i')$ hereinafter. In step S207, the processing unit 15 determines the shape of the surface to be measured based on the position coordinates $(X_i', Y_i', Z_i')$ corrected in step S206. The measurement apparatus according to the second embodiment can thus accurately measure the shape of the surface to be measured having, for example, a nonplanar shape by executing steps S201 to S207.

As described above, the measurement apparatus according to the second embodiment calculates the abrasion length A for each of the plurality of regions 8 on the surface of the leading edge portion 2, and corrects the position coordinates of each measurement point using the calculated abrasion length A. The measurement apparatus according to the second embodiment thus determines the shape of the surface to be measured based on the corrected position coordinates of each measurement point. It is therefore possible to reduce measurement errors caused by abrasion of the leading edge portion 2 of the probe 4 and accurately measure the shape of the surface to be measured.

Embodiment of Method of Manufacturing Article

A method of manufacturing an article according to an embodiment of the present invention is used to manufacture, for example, an article such as a metal part or an optical element. The method of manufacturing an article according to this embodiment includes a step of measuring the surface shape of an object to be measured using the above-described measurement apparatus, and a step of processing the object based on a measurement result in the above step. For example, the surface shape of an object to be measured is measured using a measurement apparatus, and the object is processed (manufactured) based on the measurement result such that the shape of the object has a design value. The method of manufacturing an article according to this embodiment is advantageous in at least one of the performance, quality, productivity, and production cost of the article, as compared to conventional methods because the shape of an object to be measured can accurately be measured by the measurement apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-186578 filed on Sep. 9, 2013, which is hereby incorporated by reference herein in its entirety.

What is claimed is:

1. A measurement apparatus which includes a probe having a leading edge portion configured to come into contact with a surface to be measured and a holding portion configured to hold the leading edge portion, and measures a shape of the surface by scanning the probe relative to the surface in a state in which the leading edge portion and the surface are in contact, comprising:

a processing unit configured to correct measurement data at a measurement point on the surface based on data of a scanning distance of the probe and information about abrasion of the leading edge portion caused by scanning of the probe.

2. The apparatus according to claim 1, wherein the processing unit obtains, as the data of the scanning distance, data of an accumulated distance value accumulated upon scanning the probe in a state in which the leading edge portion abrades.

3. The apparatus according to claim 1, wherein the processing unit obtains, as the information, data of a relationship between the scanning distance and an amount of a change, caused by the abrasion of the leading edge portion, in a distance between a contact point of the leading edge portion in contact with the surface and a reference point of the leading edge portion.

4. The apparatus according to claim 3, wherein in a case where the contact point moves on a surface of the leading edge portion in accordance with the shape of the surface, the processing unit determines a region including the contact point at the measurement point out of a plurality of regions on the surface of the leading edge portion, and corrects the measurement data at the measurement point based on the information and the data of the scanning distance upon scanning the probe in a state in which abrasion occurs in the determined region.

5. The apparatus according to claim 3, wherein letting A be the change amount, R be a radius of the leading edge portion, V be a volume of abrasion of the leading edge portion, L be the scanning distance of the probe, and K is a proportionality constant, the processing unit obtains the data of the relationship based on $$V = KL = \frac{1}{3}\pi A^2(3R - A)$$

when the leading edge portion has a spherical shape and is fixed to the holding portion.

6. The apparatus according to claim 5, wherein the processing unit determines the proportionality constant using the scanning distance and the change amount on at least one point of the surface in a case where the probe is scanned from an initial point on the surface through the at least one point.

7. The apparatus according to claim 3, wherein letting A be the change amount, R be a radius of the leading edge portion, V be a volume of abrasion of the leading edge portion, L be the scanning distance of the probe, and K is a proportionality constant, the processing unit obtains the data of the relationship based on $$V = KL = \frac{4}{3}\pi A^2(3R^2 - 3RA + A^2)$$

when the leading edge portion has a spherical shape and is held by the holding portion so as to rotate about a center.

8. The apparatus according to claim 7, wherein the processing unit determines the proportionality constant using the scanning distance and the change amount on at least one point of the surface in a case where the probe is scanned from an initial point on the surface through the at least one point.

9. The apparatus according to claim 3, wherein letting A be the change amount, R be a radius of the leading edge portion, V be a volume of abrasion of the leading edge portion, L be the scanning distance of the probe, and K is a proportionality constant, the processing unit obtains the data of the relationship based on $$V = KL = \frac{4}{3}\pi RA(2R - A)$$

when the leading edge portion has a spherical shape and is held by the holding portion so as to rotate about an axis passing through a center.

10. The apparatus according to claim 9, wherein the processing unit determines the proportionality constant using the scanning distance and the change amount on at least one point of the surface in a case where the probe is scanned from an initial point on the surface through the at least one point.

11. The apparatus according to claim 3, wherein the processing unit obtains the data of the relationship using data of a plurality of sets of the scanning distances and the change amounts measured using the measurement apparatus.

12. A method of manufacturing an article, the method comprising:
  measuring a surface shape of an object to be measured using a measurement apparatus; and
  processing the object based on a measurement result in the measuring;
  wherein the measurement apparatus which includes a probe having a leading edge portion configured to come into contact with a surface of the object to be measured and a holding portion configured to hold the leading edge portion, and measures a shape of the surface by scanning the probe relative to the surface in a state in which the leading edge portion and the surface are in contact, includes:
  a processing unit configured to correct measurement data at a measurement point on the surface based on data of a scanning distance of the probe and information about abrasion of the leading edge portion caused by scanning of the probe.

13. A measurement method of measuring a shape of a surface to be measured by scanning a probe having a leading edge portion configured to come into contact with the surface and a holding portion configured to hold the leading edge portion relative to the surface in a state in which the leading edge portion is in contact with the surface, the method comprising:
  obtaining information about abrasion of the leading edge portion caused by scanning of the probe;
  correcting measurement data at a measurement point on the surface based on data of a scanning distance of the probe and the information obtained in the obtaining; and
  determining the shape of the surface using the measurement data corrected in the correcting.

* * * * *